United States Patent
Levy et al.

(10) Patent No.: US 9,314,147 B2
(45) Date of Patent: Apr. 19, 2016

(54) ROTATABLE CONNECTOR FOR AN ENDOSCOPE

(71) Applicant: PEER MEDICAL LTD., Caesarea (IL)

(72) Inventors: Avi Levy, Herzliya (IL); Moshe Levi, Gane Tikva (IL); Amram Aizenfeld, Ramot Menashe (IL); Yaniv Kirma, Tzrufa (IL)

(73) Assignee: ENDOCHOICE INNOVATION CENTER LTD., Caesarea (IL)

( * ) Notice: Subject to any disclaimer, the term of this patent is extended or adjusted under 35 U.S.C. 154(b) by 173 days.

(21) Appl. No.: 13/713,466

(22) Filed: Dec. 13, 2012

(65) Prior Publication Data

US 2013/0150671 A1    Jun. 13, 2013

Related U.S. Application Data

(60) Provisional application No. 61/569,796, filed on Dec. 13, 2011.

(51) Int. Cl.
*A61B 1/00* (2006.01)
*A61B 1/04* (2006.01)
*A61B 1/12* (2006.01)

(52) U.S. Cl.
CPC .................................. *A61B 1/00121* (2013.01)

(58) Field of Classification Search
CPC ........... A61B 1/00112; A61B 1/00114; A61B 1/00117; A61B 1/00119; A61B 1/00121; A61B 1/00124; A61B 1/00126; A61B 1/00128
USPC ......... 600/132, 178–180, 112, 121–125, 131, 600/136, 155–159; 348/65–76
See application file for complete search history.

(56) References Cited

U.S. PATENT DOCUMENTS

| | | | |
|---|---|---|---|
| 4,253,448 A | 3/1981 | Terada | |
| 4,261,345 A | 4/1981 | Yamaguchi | |
| 4,402,313 A * | 9/1983 | Yabe | .............................. 600/132 |
| 4,414,608 A | 11/1983 | Furihata | |
| 4,439,030 A | 3/1984 | Ueda | |
| 4,469,090 A | 9/1984 | Konomura | |
| 4,494,549 A | 1/1985 | Namba | |

(Continued)

FOREIGN PATENT DOCUMENTS

| | | |
|---|---|---|
| CN | 1988841 | 6/2007 |
| CN | 101061940 A | 10/2007 |

(Continued)

OTHER PUBLICATIONS

International Search Report for PCT/EP2009/066726, Aug. 16, 2010.

(Continued)

*Primary Examiner* — Ryan Henderson
(74) *Attorney, Agent, or Firm* — Novel IP (57) ABSTRACT

A rotating connector formed within an endoscope console for connecting an endoscope to a console, comprising: a fixed part located on the endoscope console for attaching the rotating connector to the console; and a rotating part adapted to be attached to the at least one fixed part such that the rotating part can rotate relatively to the at least one fixed part, the rotating part also adapted to receiving an endoscope connector, wherein the rotating connector enables rotation of the endoscope while eliminating twisting of a proximal shaft connecting the endoscope to the console.

10 Claims, 7 Drawing Sheets

(56) References Cited

U.S. PATENT DOCUMENTS

| | | |
|---|---|---|
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D'Amelio et al. |
| 4,708,126 A | 11/1987 | Toda |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,852,511 A | 12/1998 | Tateyama |
| 5,870,234 A | 2/1999 | EbbesmeierneeSchitthof |
| 5,871,439 A | 2/1999 | Takahashi |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,201,646 B1 | 3/2001 | Togino |
| 6,201,648 B1 | 3/2001 | Togino |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |

(56) References Cited

U.S. PATENT DOCUMENTS

| | | |
|---|---|---|
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |

(56) References Cited

U.S. PATENT DOCUMENTS

| | | | |
|---|---|---|---|
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 2002/0007110 A1 | 1/2002 | Irion |
| 2002/0087047 A1 | 7/2002 | Remijan |
| 2002/0098732 A1 | 7/2002 | Shimizu |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |

(56) References Cited

U.S. PATENT DOCUMENTS

| | | |
|---|---|---|
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1* | 8/2009 | Yamane ............. 600/159 |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |

(56) References Cited

U.S. PATENT DOCUMENTS

| | | |
|---|---|---|
| 2009/0287192 A1 | 11/2009 | Vivenzio |
| 2009/0290236 A1 | 11/2009 | Wang |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 201108422 Y | 9/2008 |
| CN | 101396258 | 4/2009 |
| CN | 101061940 | 6/2011 |
| DE | 102005008153 A1 | 11/2005 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2352922 A | 2/2001 |
| JP | 55078932 | 6/1980 |
| JP | 61055657 | 11/1986 |
| JP | 5049000594 | 3/1993 |
| JP | 6105000800 | 4/1994 |

(56) References Cited

FOREIGN PATENT DOCUMENTS

| | | |
|---|---|---|
| JP | 7000000352 | 1/1995 |
| JP | 3765500 | 7/1995 |
| JP | 8122000657 | 5/1996 |
| JP | 1013007179 | 4/1998 |
| JP | 1015001113 | 6/1998 |
| JP | 11137512 | 5/1999 |
| JP | 1116009340 | 6/1999 |
| JP | 1116009341 | 6/1999 |
| JP | 2000171727 A | 6/2000 |
| JP | 2001061762 | 3/2001 |
| JP | 2001198086 | 7/2001 |
| JP | 2002000559 | 1/2002 |
| JP | 2002058636 | 2/2002 |
| JP | 2002065575 | 3/2002 |
| JP | 2002078675 | 3/2002 |
| JP | 2002216902 | 8/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2005013557 A | 1/2005 |
| JP | 2005058547 | 3/2005 |
| JP | 2005253543 | 9/2005 |
| JP | 2006068109 A | 3/2006 |
| JP | 2006218155 | 8/2006 |
| JP | 2007020866 A | 2/2007 |
| JP | 2007185276 | 7/2007 |
| JP | 2008161569 A | 7/2008 |
| JP | 2008229204 | 10/2008 |
| JP | 2009233186 | 10/2009 |
| JP | 4445647 | 4/2010 |
| JP | 2010178766 A | 8/2010 |
| JP | 2010279539 | 12/2010 |
| WO | 0029555 A2 | 6/1981 |
| WO | 9219148 A1 | 11/1992 |
| WO | 0052643 A1 | 9/2000 |
| WO | 0245595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010028612 | 3/2010 |
| WO | 2010045406 | 4/2010 |
| WO | 2010066788 | 6/2010 |
| WO | 2010146587 | 12/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013131578 | 9/2013 |
| WO | 2013144944 | 10/2013 |
| WO | 2014061023 | 4/2014 |

OTHER PUBLICATIONS

Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
Office Action dated Feb. 27, 2014 for U.S. Appl. No. 13/557,114.
Second Image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
International Search Report of PCT/IL2011/000745, dated May 8, 2012.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.
International Search Report of PCT/IL10/00476 mailed Sep. 27, 2010, 2 pages.
Office Action dated Apr. 3, 2014 for U.S. Appl. No. 13/413,141.
Office Action dated Feb. 24, 2014 for U.S. Appl. No. 13/190,968.
Office Action dated Jul. 1, 2014 for U.S. Appl. No. 13/655,120.
Office Action dated Jul. 31, 2014 for U.S. Appl. No. 13/713,449.
Office Action dated Mar. 28, 2014 for U.S. Appl. No. 13/413,252.
Office Action dated May 27, 2014 for U.S. Appl. No. 13/212,627.
Office Action dated May 30, 2014 for U.S. Appl. No. 13/119,032.
Office Action dated May 9, 2014 for U.S. Appl. No. 13/413,059.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Supplementary European Search Report for European Application No. EP12823972, May 13, 2015.
Extended European Search Report for EP14186113.8, Apr. 1, 2015.
Corrected European Search Opinion for EP14186113.8, Apr. 29, 2015.

* cited by examiner

ROTATABLE CONNECTOR FOR AN ENDOSCOPE

FIELD OF THE INVENTION

Embodiments of the disclosure relate to a rotatable connector for an endoscope.

BACKGROUND OF THE INVENTION

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having one or more video cameras, fiber optic lens assemblies, or any other capturing device at its distal end or more proximally on or near the lateral surface area of the tip section. Various surgical tools may be inserted through a working channel and used near the endoscope distal end for performing different surgical procedures. The endoscope distal end or its surrounding may also comprise one or more openings through which air, water or another gas, fluid or liquid may be injected through the endoscope and into the body cavity, for purposes such as cleaning the body cavity, applying suction in order to evacuate various liquids or solids that interfere with the inspection, inflating the body cavity which may be beneficial for cases in which the body cavity, such as the colon, is shriveled or otherwise does not allow for efficient inspection, or the like.

The shaft is connected to a handle, which may include controls for operating the endoscope or an ocular for direct viewing. Viewing may also be possible via an external screen.

The endoscope may receive supplies by connecting the endoscope handle to one or more consoles providing water, air, or any other gas, fluid or liquid, or suction. Also passed through the endoscope shaft are cables such as electric wires, optic fibers, video cables or the like, for transferring signals or energy to and from the endoscope. The signals may also be received from one or more consoles, which may be the same console as the one supplying fluids or liquids, or a different one.

There is a need in the art for endoscopes, such as colonoscopies, that allow more convenient operation to the operator, and safer structure for protecting the sensitive components of the endoscope as well as the operator, such as fiber optics electrical systems, or the like.

SUMMARY OF THE INVENTION

One aspect of the disclosure relates to a rotating connector formed within an endoscope console for connecting an endoscope to a console, comprising: one or more fixed parts located on the endoscope console for attaching the rotating connector to the console; and a rotating part adapted to be attached to any one or more of the fixed parts, such that the rotating part can rotate relatively to the fixed part, the rotating part also adapted to receiving an endoscope connector, wherein the rotating connector enables rotation of the endoscope while essentially eliminating or reducing twisting of a proximal shaft connected to the endoscope. In some embodiments of the rotating connector the fixed part may comprise a housing for covering at least partially the rotating part. In some embodiments of the rotating connector, the rotating part may comprise a cylindrical opening adapted to receive one or more pins protruding from the endoscope connector. In some embodiments of the rotating connector the rotating part may comprise a cylindrical opening adapted to receive a tube for passing gas, fluid or liquid to the endoscope connector. In some embodiments of the rotating connector, the fixed part may comprise a recess and the rotating parts may comprise a protruding part so that movement of the moving part within the recess limits the rotation of the rotating part. In some embodiments of the rotating connector the rotation of any of the rotating parts may be limited to about 90°. In some embodiments of the rotating connector, the fixed parts may comprise a disk. In some embodiments of the rotating connector the disk may comprise a recess for containing gas, fluid or liquid over flow, and a gasket for sealing a gap between the disk and the at least one rotating part.

Another aspect of the disclosure relates to a connector for connecting an endoscope to an endoscope console, comprising: a connector connected to a proximal shaft of the endoscope and adapted to be inserted into a rotating connector located on the endoscope console, wherein the connector and the rotating connector are adapted to enable rotation of the endoscope while eliminating twisting of a proximal shaft connecting the endoscope to the console. In some embodiments the connector may further comprise a protruding part adapted to be inserted into a recess in the rotating connector. In some embodiments the connector may further comprise a cannula for receiving flow of gas, liquid or fluid supplied from the console via a tube contained within the rotating connector.

Yet another aspect of the disclosure relates to an endoscope console comprising a rotating connector adapted for receiving an endoscope connector, the rotating connector comprising: one or more fixed parts located on the endoscope console for attaching the rotating connector to the console; and a rotating part adapted to be attached to one or more of the fixed parts such that the rotating part can rotate relatively to the fixed part, the rotating part also adapted to receiving an endoscope connector, wherein the rotating connector enables rotation of the endoscope while essentially eliminating or reducing twisting of a proximal shaft connected to the endoscope.

Yet another aspect of the disclosure relates to a connector designed to connect an endoscope and an endoscope console, comprising: one or more first parts adapted to be connected to the endoscope console; and one or more second parts adapted to be connected to the endoscope, wherein one of the first parts can rotate relatively to one or more of the second parts. In some embodiments of the connector one of the first parts may comprise two or more parts which may not rotate relatively to each other. In some embodiments of the connector, one or more of the second parts may comprise two or more parts which may not rotate relatively to each other.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

An aspect of some embodiments of the disclosure relates to a rotating connector, connected to an endoscope console, and adapted to receive an endoscope connector, so that rotations applied to the endoscope may be released and do not cause the endoscope proximal shaft cable to become twisted.

One technical problem addressed by the disclosed subject matter relates to the rotations and twists applied to the endoscope handle during operation.

When an operator uses an endoscope, he or she may be turning and twisting the endoscope handle when navigating within the body cavity into which the endoscope is inserted. Repeated twisting and handling may accumulate to substantial twisting of the endoscope proximal shaft, may eventually damage the proximal shaft connecting the endoscope handle to the console, or any of the tubes, cords or fibers going through the proximal shaft. Such twisting may shorten the available length of the proximal shaft, and may reduce the flexibility and ease with which the operator can use the device, thus harming its efficiency. However, in addition to releasing the rotation, it is required to provide continuous supply of gas, liquid, fluid, or suction to the endoscope, or to transfer signals or energy to or from the endoscope without having the supply interrupted by the rotation or the release thereof.

One technical solution is the provisioning of a rotating connector which connects on one side to the endoscope console, and on the other to the endoscope proximal shaft. The rotating connector provides for avoiding twists while ensuring continuous provisioning of gas, liquid, fluid or suction to the endoscope. Using the rotating connector, twists and turns applied to the endoscope handle are essentially, not formed, released and/or do not accumulate, so the endoscope proximal shaft does not become twisted or tangled.

One technical effect of the disclosed subject matter is the elimination of twists of an endoscope proximal shaft, thus avoiding damage to the proximal shaft or to fibers, cords or tubes going through the proximal shaft. A further advantage of the rotating connector is the elimination of the shortening of the proximal shaft, thus providing for enhanced ease and comfort to a user, and greater functionality. Yet, the rotating connector provides for continuous supply of gas, liquid, fluid, to the endoscope.

Another technical effect of the disclosed subject matter is that since the rotating connector is attached to the endoscope console, fewer parts are rotating, compared for example to systems in which the connector used for releasing the twists is located on the endoscope handle. In particular, no cords or fibers are twisted which reduces their wear and tear, keeps them at better state, and improves the maintainability of the endoscope system.

Yet another technical effect of the disclosed subject matter is that the provisioning of the release mechanism on the endoscope console, rather than on the endoscope handle or another part held by an operator, eliminates the need to carry further weight by the operator, and enhances operation simplicity.

Figure 1:
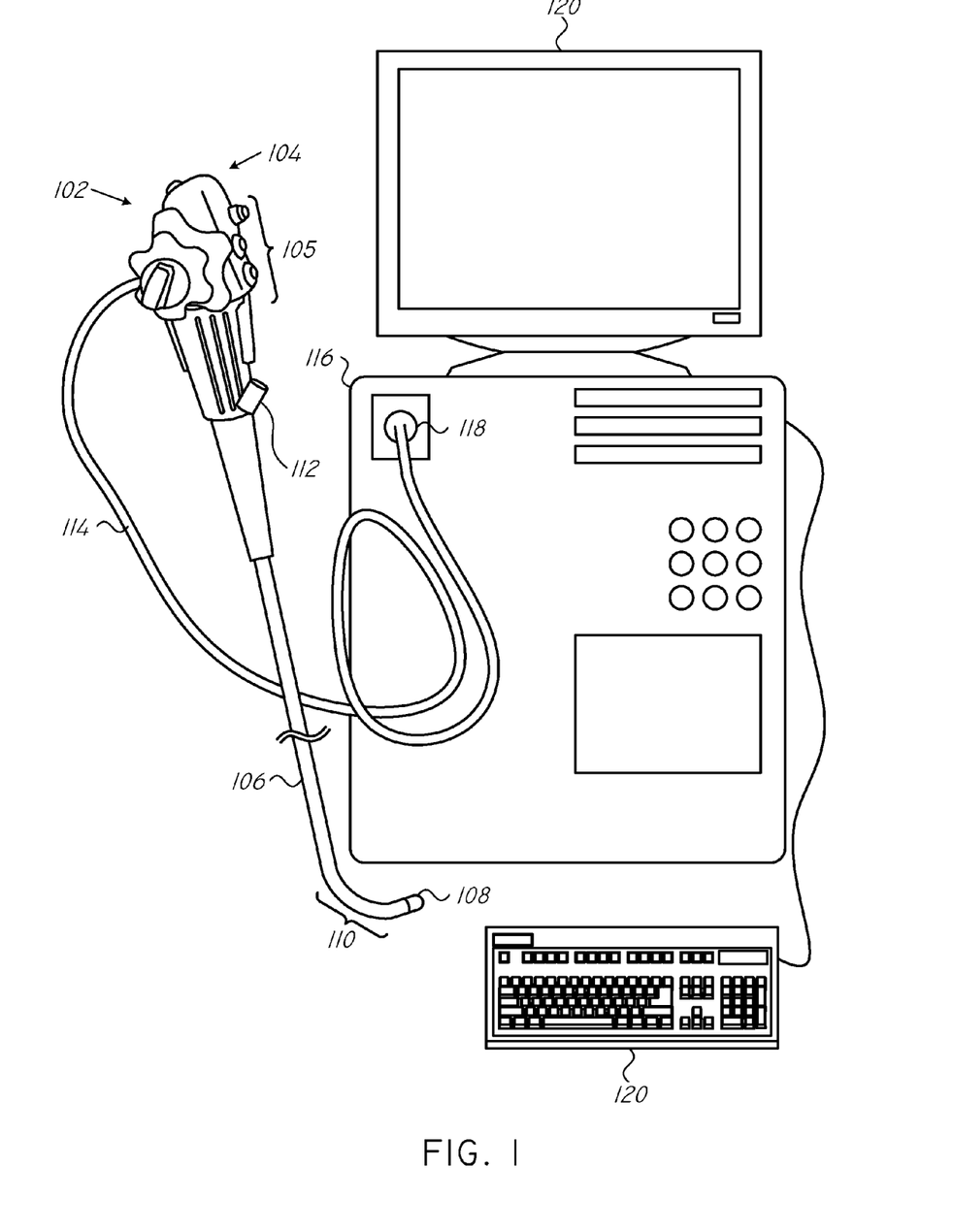
FIG. 1 shows a semi-pictorial view of an endoscopy system.

Referring now to FIG. 1, showing a semi-pictorial view of an endoscopy system 100. System 100 may include endoscope 102. Endoscope 102 may include a handle 104, from which an elongated shaft 106 emerges. Elongated shaft 106 terminates with a tip section 108 which may be turnable by way of a bending section 110.

Tip 108 may include one or more capturing devices such as a camera, one or more internal or external illuminators, i.e., an illuminator which produces light, or an illuminator which reflects light produced elsewhere, an opening for a surgical tool, a fluid or liquid injector, or the like.

Handle 104 may be used for maneuvering elongated shaft 106 within a body cavity by pushing, pulling, rotating or other motions; the handle may include one or more knobs and/or switches 105 which control bending section 110 as well as endoscopic functions such as fluid or liquid injection, or suction. Handle 104 may further include one or more working channel openings such as working channel opening 112 through which surgical tools may be inserted which may then be used in the vicinity of endoscope tip 108 within the body cavity.

One or more cables or tubes such as proximal shaft 114 may connect between handle 104 and one or more consoles such as console 116. Proximal shaft 114 may include therein one or more fluid channels, one or more electrical or data channels, optic fibers or the like. The electrical channel(s) may include at least one data cable for receiving visual signals such as video signals from a capture device located on tip 108, as well as one or more power cables for providing electrical power to the capture devices or to the illuminators. Proximal shaft 114 may connect to console 116 using a connector 118.

Console 116 may govern power transmission to endoscope's 102 tip section 108, such as for the tip section's capture devices and illuminators. Console 116 may further provide one or more gas, fluid, liquid and/or suction pump which provide corresponding functionalities to endoscope 102. One or more input devices, such as a keyboard 120 may be connected to console 116 for the purpose of human interaction with the controller. In another configuration (not shown), an input device, such as a keyboard, may be integrated with the console in the same casing.

A display 120 may be connected to or embedded within console 116, and configured to display images and/or video streams received from the cameras of tip 108. Display 120 may further be operative to display a user interface for allowing a human operator to set various features or parameters of system 100.

Optionally, the image streams received from the one or more cameras of endoscope 102 may be displayed on display 120. If endoscope 102 comprises multiple cameras, the images may be displayed on display 120 side-by-side, interchangeably (namely, the operator may switch between views from the different cameras manually), or in any other manner. Alternatively, the video streams may be processed by console 116 to combine them into a single video frame which may be panoramic or three-dimensional, based on an overlap between fields of view of the cameras or on known coordinates obtained for example from fiducials. In another configuration (not shown), two or more displays may be connected to console 116, each for displaying a video stream from a different camera of the multi-camera endoscope.

It will be appreciated that handle 104 may be connected to two or more consoles, each providing one or more different functionalities of the endoscope. For example, a first console may provide liquids, fluids, and suction while another console may provide electric power and receive video images.

Figure 2:
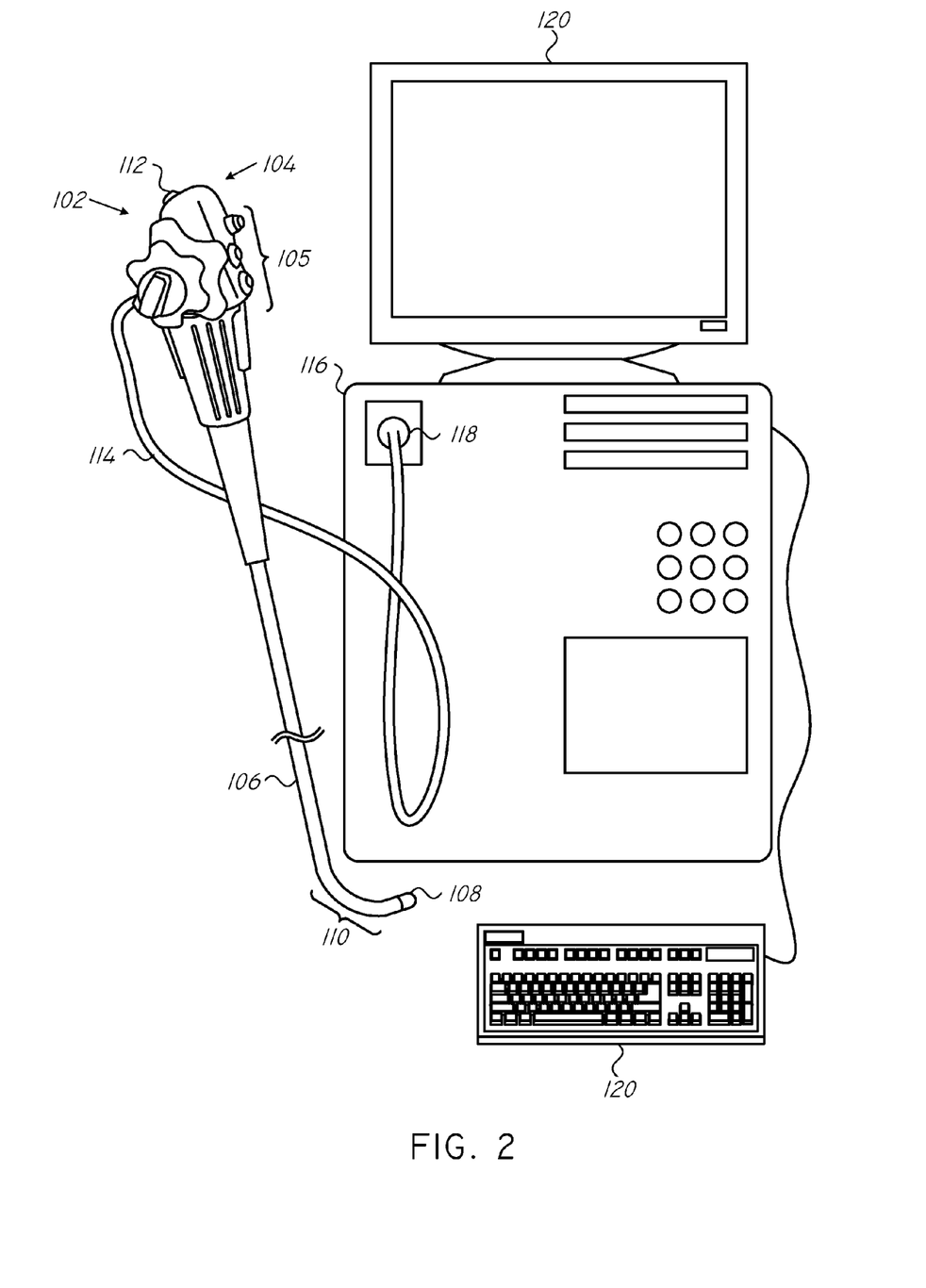
FIG. 2 shows a semi-pictorial view of an endoscopy system with a twisted proximal shaft.

Referring now to FIG. 2, showing the endoscope of FIG. 1, wherein the proximal shaft is highly twisted.

The endoscope of FIG. 2 may have been used for some period of time by an operator, who turned and rotated and twisted endoscope handle 104, and caused Proximal shaft 114 to twist and entangle.

For illustration purposes only, the entangling effect may be similar to what may happen to a phone handset connected to the base station when the cord entangles. However, an endoscope proximal shaft, due for example to the stiff tubes, may bear much less twisting. After twisting the endoscope may become less comfortable to use and the operator may have lesser flexibility and freedom to operate the endoscope.

Figure 3:
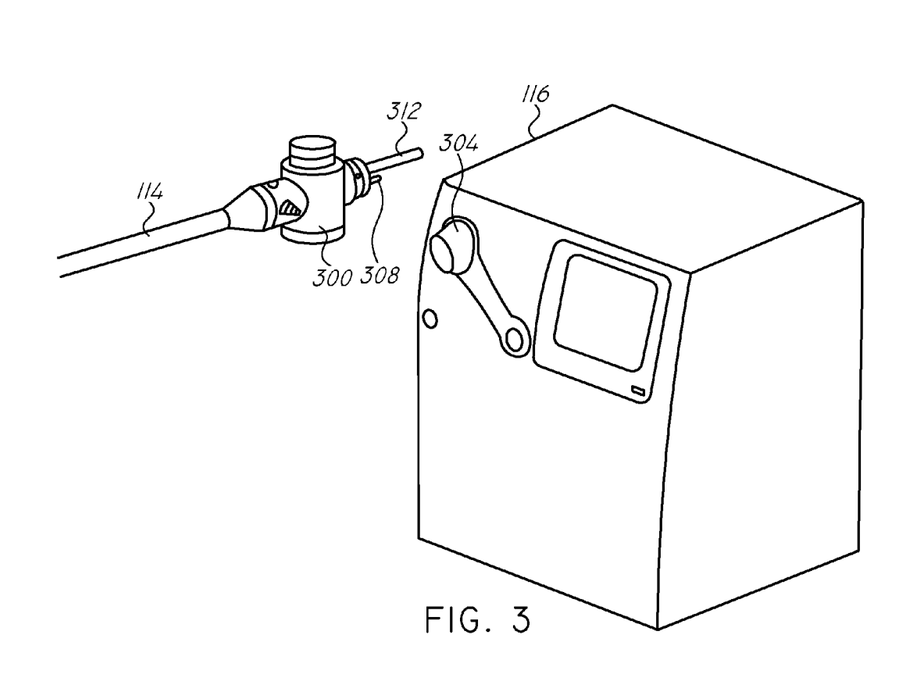
FIG. 3 shows a perspective view of an endoscope proximal shaft to be connected to a console via a rotating connector, in accordance with some exemplary embodiments of the disclosure.

Referring now to FIG. 3, showing a perspective view of an endoscope proximal shaft to be connected to a console via a rotating connector.

FIG. 3 shows proximal shaft 114, connected to connector 300. Connector 300 has protruding therefrom a short pipe or cannula 308 and a pin 312. Connector 300 may be connected to the rotating connector of the endoscope console (not shown) having external housing 304. The Rotating connector, exemplary embodiments of which are detailed in association with FIG. 5 and FIG. 6 below, has one or more rotating parts and one or more fixed parts. The fixed parts, including housing 304, are attached to console 116 and do not rotate. Thus, when proximal shaft 114 is rotated, connector 300 and the rotating parts of the rotating connector of the endoscope console rotate with it, but the rotation is released by the relative movement enabled between the rotating parts and the fixed parts of the rotating connector of the endoscope console, and thus proximal shaft 114 is prevented from twisting.

It will be appreciated that in some embodiments, the relative movement between the rotating part and the fixed part of the rotating connector may be limited to a predetermined angle, which is in accordance with the operational requirements of the endoscope. This angle limitation is also detailed on association with FIG. 5 and FIG. 6 below.

Figure 4A:
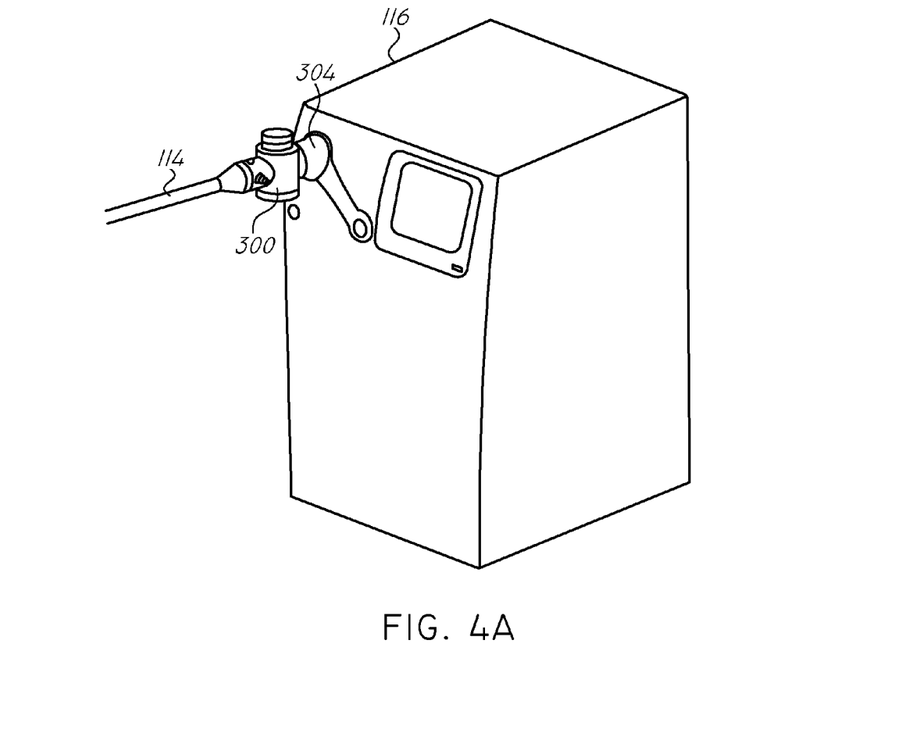
FIGS. 4A-4C show perspective views of an endoscope proximal shaft rotated in various angles and connected to a console via a rotating connector, in accordance with some exemplary embodiments of the disclosure.
Figure 4B:
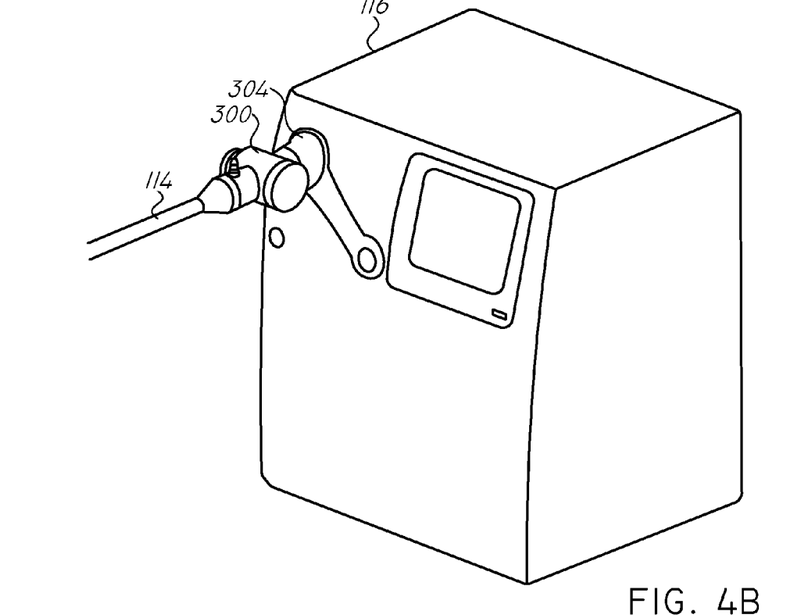
Figure 4C:
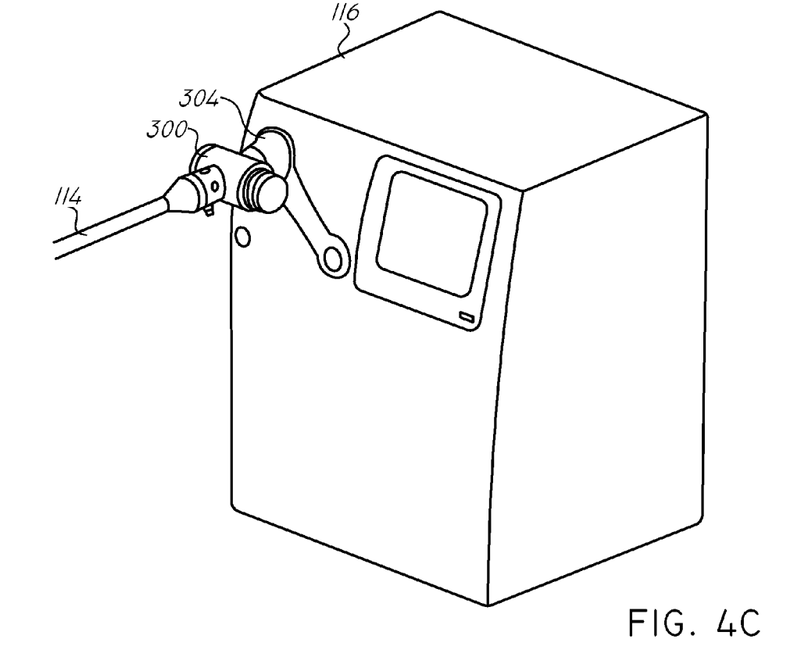

Referring now to FIGS. 4A-4C, showing connector 300 as connected to the rotating connector of the endoscope console (shown by housing 304). As seen in FIGS. 4A-4C, connector 300 may rotate due to rotation of proximal shaft 114, which may be caused by the operator maneuvering the endoscope handle. Connector 300 is 90° apart between FIG. 4A and FIG. 4B, and between FIG. 4B and FIG. 4C. Connector 300 thus rotates, and so do the rotating parts of the rotating connector of the endoscope console. However, the fixed parts of rotating console connector such as housing 304, do not rotate. Thus, the proximal shaft may be rotated, but it may not become twisted, and continuous provisioning of supplies to the endoscope is not interrupted.

Figure 5:
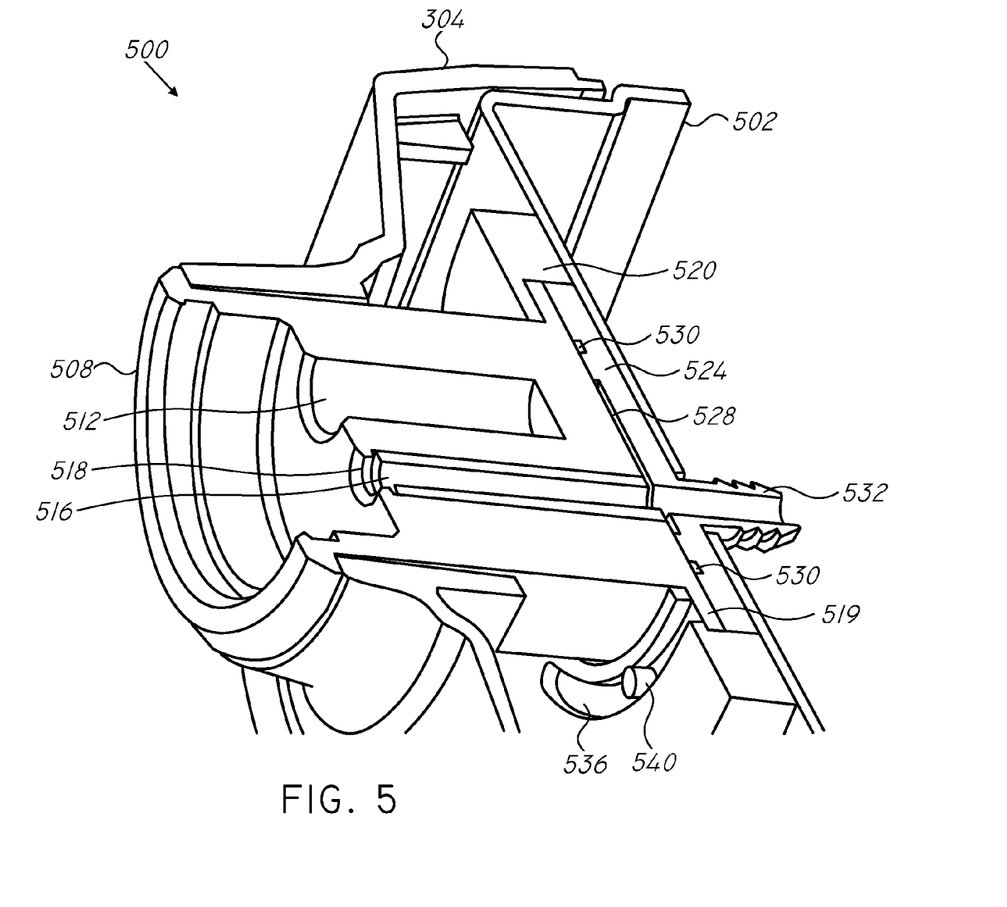
FIG. 5 shows a perspective cross section of a rotating connector of an endoscope console, in accordance with some exemplary embodiments of the disclosure.

Referring now to FIG. 5, showing an exemplary embodiment of perspective cross section of a rotating connector of an endoscope console.

The connector, generally referenced 500 comprises rotating part 508, adapted to receive connector 300 which may connect to the endoscope proximal shaft. Thus, rotating part 508 comprises a cylindrical opening 512 adapted to receive pin 312 of connector 300, and cylindrical opening 518 which may be adapted to contain within a tube or cannula 516. Pin 312, when inserted into cylindrical opening 512, may be used for stabilizing the endoscope connector within the rotating connector. When connector 300 is inserted into rotating part 508, tube 308 is inserted into the end of cannula 516, thus providing gas, fluid or liquid passed through cannula 316 to the endoscope. Rotating part 508 may also comprise rotating base 519.

While rotating part 508 may rotate when connector 300 is connected thereto and rotates, other parts of connector 500 may be fixed and do not rotate.

One fixed part is base 502, which connects or attaches rotating connector 500 to console 116, and another fixed part is housing 304 which substantially covers at least the sides of rotating connector 500. Cannula 516 located within rotating part 508 is in continuation, or in proximity to tube 532 which penetrates through base 502 and receives supplies from console 116, such as air, water, other liquid or fluid, suction, light, or the like.

The fixed parts may also include disk 524 which may be connected to base 502. Disk 524 may have therein a recess 528. When gas, fluid or liquid flows from console 116 through tube 532 into cannula 516, overflows may collect in recess 528. Disk 524 may also have a peripheral recess 530 which may contain a sealing material or a gasket, for sealing the gap between disk 524 and rotating base 519, in order to eliminate the gas, fluid or liquid from spreading around.

Thus, when rotating part 508 rotates together with connector 300, cannula 516 may not be aligned with tube 532, but the fluid or gas will still collect in recess 528 and flow uninterruptedly into tube cannula, tube 308 and into the endoscope.

Base 519 and disk 524 may be held together using cover 520. Cover 520 may comprise a recess 536 which may stretch along a predetermined part of the perimeter, for example 90° of the perimeter. Rotating base 519 may be equipped with a knob or another protrusion 540 which is placed within recess 536, so that the rotation of rotating part 508, as well as connector 300, is limited to the movement of protrusion 540 within recess 536.

It will be appreciated that the perimeter of base 502, housing 504, rotating part 508, cover 520 and disk 524 may be shaped substantially as a circle, in order to provide for convenient rotation of rotating part 508 relatively to the fixed parts.

It will be that appreciated by a person skilled in the art that rotating part 508 and connector 300 are constructed with corresponding structures, such as to provide secure lock and convenient release.

Figure 6:
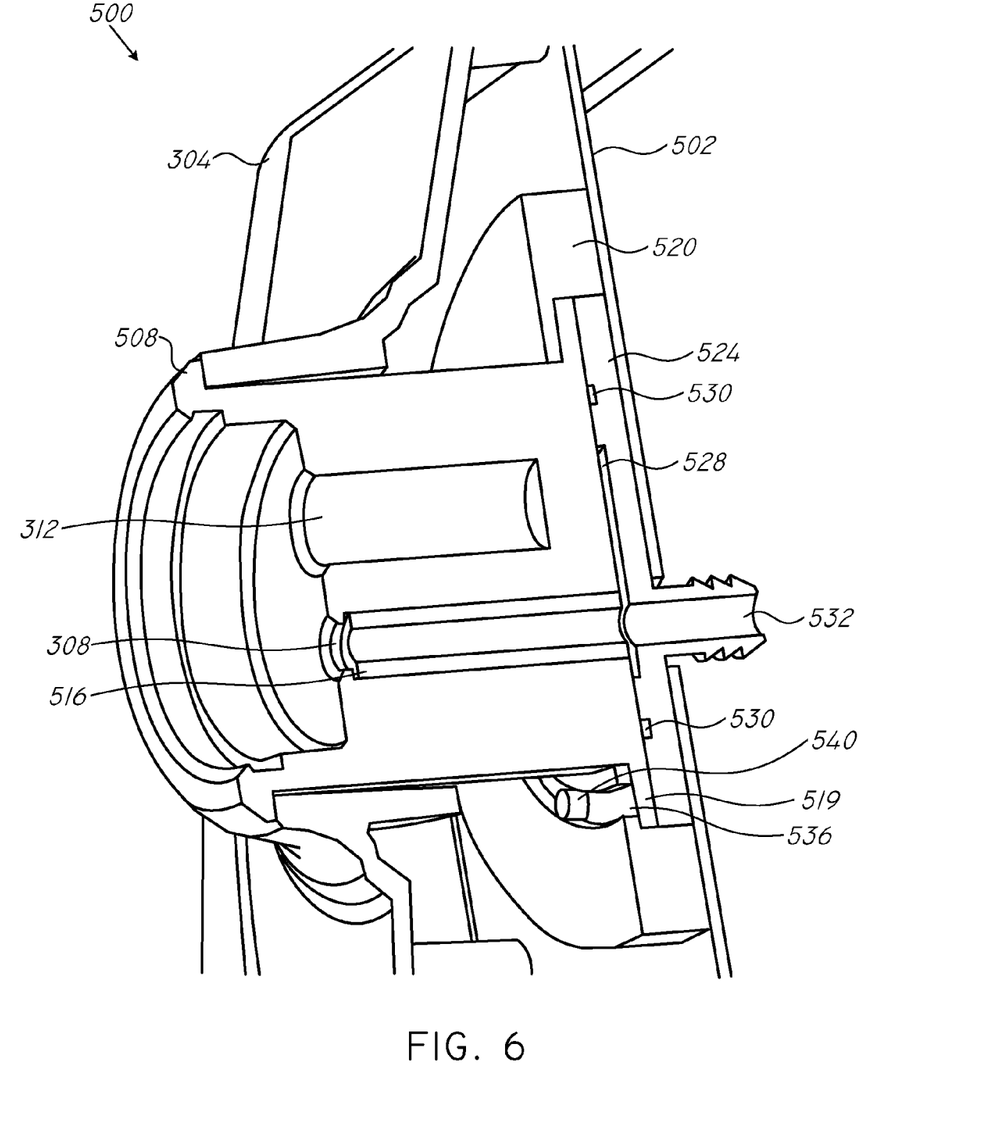
FIG. 6 shows a perspective cross section of an endoscope connector connected to a rotating connector of an endoscope console, in accordance with some exemplary embodiments of the disclosure.

Referring now to FIG. 6, showing another view of a cross section of a rotating connector of an endoscope console.

Endoscope connector 500 comprises rotating part 508 which is adapted to receive connector 300, such that when connector 300 is connected to the endoscope, tube 308 protruding from connector 300 is inserted into cannula 516, and pin 312 is inserted into recess 512.

Endoscope connector 500 further comprises fixed base 502, which connects or attaches rotating connector 500 to console 116, housing 304 which substantially covers at least the sides of rotating connector 500, and cover 520. Cover 520 comprises recess 536, in which knob 540 of rotating base 519 can move.

Figure 7:
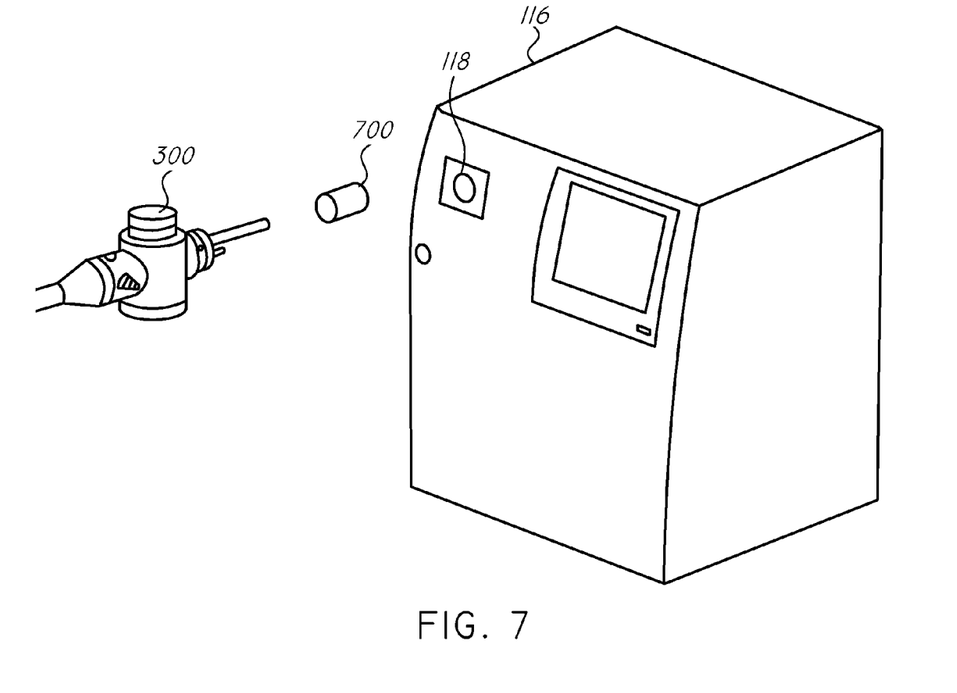
FIG. 7 shows a perspective view of a rotating connector for an endoscope, in accordance with some exemplary embodiments of the disclosure.

Referring now to FIG. 7, showing another embodiment of a rotating connector for an endoscope.

FIG. 7 shows endoscope connector 300 and console 116. Connector 700 is designed to connect on one side to connector 300, and on the other side to console 116 having connections as known in the art.

Connector 700 may comprise therein at least two groups of parts: a first group of parts which may connect to connector 300, and a second group of parts which may connect to console 116 through connector 118, such that parts of the first group do not rotate relatively to each other, parts of the second group also do not rotate relatively to each other, but the first group rotates relatively to the second group. Connector 700 can be designed such that the parts connecting to condole 116 are similar to the fixed parts of connector 500, e.g. fixed base 502, housing 304 and cover 520. The parts connectable to connector 300 may be designed to be similar to rotating part 508 of connector 500 and additional parts that rotate with it.

This embodiment enables immediate adaptation of any endoscope to the rotating connector, so that no changes are required to be made to the endoscope or to the console.

The disclosed connectors provide for eliminating torsion and twist of an endoscope proximal shaft when the endoscope is rotated, while providing uninterrupted supply of gas, liquid or fluid, and without twisting tubes or other parts which may harm them, which provides for easier maintenance and enhanced ease of use.

The disclosed connectors can be used for eliminating twisting in any existing endoscope and console. By providing a connector 300 which connects to the endoscope proximal shaft, and providing a rotating connector 500 to the endoscope console, any existing endoscope can be connected to a console which provides the necessary supplies.

In some exemplary embodiments, by designing rotating connector 500 such that cylindrical opening 518 is in continuation to tube 532, an electric wire or optic fiber may pass through tube 532 and cylindrical opening 518, and may connect using a corresponding rotating plug to a wire or fiber passing through connector 300. Thus, signals may be passed from the endoscope console to the endoscope without twisting the proximal shaft or any cables and harming them.

It will be appreciated that endoscope handle 104 can be connected to two or more consoles such as console 116, using a corresponding number of instances of connector pairs such as endoscope connector 300 and rotating connector 500. Thus, the endoscope can be connected to a first console supplying gas, fluid, liquid, suction, or the like, a second consoles supplying electric power and optic fibers, or the like. Using the disclosed connectors provides for twist-free proximal shaft and cables connecting the endoscope to each of the consoles.

It will also be appreciated that the disclosed connectors are exemplary only, and that various modifications and alternative embodiments can be designed to enable the rotation of an endoscope proximal shaft without making it twisted, and without interrupting the supply flow to the endoscope.

While a number of exemplary embodiments and configurations have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A rotating connector positioned on an endoscope console for connecting an endoscope to the endoscope console, wherein the endoscope console comprises a tube for delivering gas or fluid, comprising:

at least one fixed part located on the endoscope console for causing the rotating connector to contact the console, wherein the at least one fixed part comprises a base, a cover and a non-rotating planar disk having an opening in fluid communication with said tube, wherein the cover is attached to the base and comprises a recess extending around a periphery of thereof, and wherein the non-rotating planar base is positioned between the cover and the base;

a rotating part adapted to contact the at least one fixed part such that the rotating part can rotate relatively to the at least one fixed part, wherein;

a first end of the rotating part comprises a cylindrical opening adapted to receive a member of an endoscope and a cannula adapted to receive a tube of the endoscope and configured to receive the gas or fluid from the tube in the console and deliver said gas or fluid into the tube of the endoscope;

a second end of the rotating part comprises a rotating planar base having an opening in fluid communication with said cannula, said rotating planar base being positioned between the cover and the non-rotating planar disk such that the rotating planar base is adapted to rotate between the cover and the non-rotating planar disk; and the rotating planar base comprises a protrusion positioned within the recess extending around the periphery of the cover such that said recess limits an extent of rotational movement of the rotating planar base by blocking a movement of the protrusion; and a second recess positioned between said non-rotating planar disk and said rotating planar base, wherein the recess is adapted to receive said gas or fluid from the tube of the console and deliver said gas or fluid to the opening in the rotating planar base in fluid communication with the cannula.

2. The rotating connector according to claim 1, further comprising a housing for covering a plurality of sides of the rotating connector.

3. The rotating connector according to claim 1, wherein said member of an endoscope is at least one pin protruding from a proximal end of the endoscope.

4. The rotating connector according to claim 1, wherein the rotation of the at least one rotating part is limited to about 90 degrees.

5. The rotating connector according to claim 1, wherein the non-rotating planar disk comprises a gasket for sealing a gap between the non-rotating planar disk and the rotating part.

6. An endoscope console, having a tube for delivering gas or fluid, comprising:

a rotating connector adapted for receiving an endoscope connector, the rotating connector comprising:

at least one fixed part located on the endoscope console for causing the rotating connector to contact the console, wherein the at least one fixed part comprises a cover and a non-rotating planar disk having an opening in fluid communication with said tube, wherein the cover is attached to the console and comprises a recess extending around a portion thereof;

a rotating part adapted to contact the at least one fixed part such that the rotating part can rotate relative to the at least one fixed part, wherein:

a first end of the rotating part comprises a cylindrical opening adapted to receive a member of an endoscope;

a second end of the rotating part comprises a rotating planar base having an opening in fluid communication with said cannula, said rotating planar base being positioned between the cover and the non-rotating planar disk such that the rotating planar base is adapted to rotate between the cover and the non-rotating planar disk; and the rotating planar base comprises a protrusion positioned within the recess extending around the periphery of the cover such that said recess limits an extent of rotational movement of the rotating planar base by blocking a movement of the protrusion; and a second recess positioned between said non-rotating planar disk and said rotating planar base, wherein the recess is adapted to receive said gas or fluid from the tube of the console and deliver said gas or fluid to the opening in the rotating planar base in fluid communication with the cannula when the tube of the console and cannula are not aligned due to a rotation of the endoscope.

7. The endoscope console of claim 6 wherein the at least one fixed part comprises at least two parts which may not rotate relatively to each other.

8. The endoscope console of claim 6, wherein said member of an endoscope is at least one pin protruding from a proximal end of the endoscope.

9. The endoscope console of claim 6, wherein the extent of rotational movement of the rotating part is limited to about 90 degrees.

10. The endoscope console of claim 6, wherein the non-rotating planar disk comprises a gasket for sealing a gap between the non-rotating planar disk and the rotating part.

* * * * *